(12) United States Patent
Belli

(10) Patent No.: US 7,585,513 B2
(45) Date of Patent: *Sep. 8, 2009

(54) LONG-LASTING STYLING MOUSSE

(75) Inventor: Emmanuelle Belli, Asnières (FR)

(73) Assignee: L'Oreal, Paris (FR)

( * ) Notice: Subject to any disclaimer, the term of this patent is extended or adjusted under 35 U.S.C. 154(b) by 579 days.

This patent is subject to a terminal disclaimer.

(21) Appl. No.: 11/000,948

(22) Filed: Dec. 2, 2004

(65) Prior Publication Data

US 2005/0095207 A1    May 5, 2005

Related U.S. Application Data

(60) Continuation of application No. 10/378,825, filed on Mar. 5, 2003, now abandoned, which is a division of application No. 09/986,122, filed on Nov. 7, 2001, now abandoned.

(30) Foreign Application Priority Data

Nov. 7, 2000 (FR) .................................. 00 14232

(51) Int. Cl.
- *A61K 8/02* (2006.01)
- *A61K 8/00* (2006.01)
- *A61K 8/18* (2006.01)
- *A61K 8/81* (2006.01)
- *A61Q 5/00* (2006.01)
- *A61Q 5/06* (2006.01)

(52) U.S. Cl. ................. 424/401; 424/70.15; 424/70.16; 424/70.1

(58) Field of Classification Search ................ 424/70.1, 424/70.15, 70.16, 401
See application file for complete search history.

(56) References Cited

U.S. PATENT DOCUMENTS

| | | | |
|---|---|---|---|
| 6,039,933 | A | 3/2000 | Samain et al. |
| 6,410,005 | B1 | 6/2002 | Galleguillos et al. |

FOREIGN PATENT DOCUMENTS

| | | |
|---|---|---|
| WO | WO 00/39176 | 7/2000 |
| WO | WO 00/40628 | 7/2000 |

*Primary Examiner*—Sreeni Padmanabhan
*Assistant Examiner*—Samira Jean-Louis
(74) *Attorney, Agent, or Firm*—Nixon & Vanderhye P.C.

(57) ABSTRACT

The invention relates to a styling composition, packaged in an aerosol device, containing: a liquid phase containing, in a cosmetically acceptable liquid medium, at least one fixing film-forming polymer chosen from branched block copolymers containing, as main monomers, at least one $C_{1-20}$ alkyl acrylate and/or at least one N-mono- or N,N-di($C_{2-12}$ alkyl) (meth)acrylamide, and acrylic acid and/or methacrylic acid, and at least one propellant.

4 Claims, No Drawings

LONG-LASTING STYLING MOUSSE

The present application is a continuation of application Ser. No. 10/378,825, filed Mar. 5, 2003 (now abandoned), which is a divisional of application Ser. No. 09/986,122, filed Nov. 7, 2001 (abandoned), the entire contents of each of which is hereby incorporated by reference.

The present invention relates to a styling mousse comprising a specific type of branched acrylic block copolymer packaged in an aerosol device.

Although a very large number of fixing polymers are recognized in the field of hair styling, most of them have a fixing power which is limited over time and which exhibits poor resistance to moisture.

The highly advantageous styling properties of a specific group of branched acrylic block copolymers, described in more detail below, have recently been discovered.

These copolymers, used in styling compositions, exhibit a combination of physicochemical and cosmetic properties which make them excellent fixing polymers. Thus, these block copolymers spread readily over the hair, exhibit good adhesion to the hair fibres, give a feel which is not very sticky, are easily removed on shampooing and give satisfactory fixing. The fixing has good elasticity, is stable over time and is particularly highly resistant to moisture.

The Applicant Company has discovered that these polymers lend themselves perfectly well to packaging in the form of a styling mousse in aerosol devices.

The significance of this is that styling mousses, a formulation generally much appreciated by users, exhibit the disadvantage of exhibiting insufficient hold over time.

In point of fact, the novel fixing acrylic block polymers indicated above, when they are packaged in the form of an aerosol composition, give styling mousses having satisfactory fixing properties and exhibiting very good hold over time. In addition, the cosmetic properties are good.

In one embodiment, the present invention relates to a composition in the form of a styling mousse, packaged in an aerosol device, comprising a liquid phase comprising, in a cosmetically acceptable liquid medium, (a) at least one fixing film-forming polymer chosen from branched block copolymers comprising, as main monomers, at least one $C_{1-20}$ alkyl acrylate and/or at least one N-mono- or N,N-di($C_{2-12}$ alkyl) (meth)acrylamide, and acrylic acid and/or methacrylic acid, and (b) at least one other fixing film-forming polymer other than the branched block copolymers (a), and at least one propellant.

In another embodiment, the present invention relates to a composition in the form of a styling mousse, packaged in an aerosol device, comprising a liquid phase comprising, in a cosmetically acceptable liquid medium, (a) at least one fixing film-forming polymer chosen from branched block copolymers comprising, as main monomers, at least one $C_{1-20}$ alkyl acrylate and/or at least one N-mono- or N,N-di($C_{2-12}$ alkyl) (meth)acrylamide, and acrylic acid and/or methacrylic acid, and at least one cationic, anionic or zwitterionic surface-active agent or a mixture of these, and at least one propellant.

The fixing film-forming polymer (a) used in the cosmetic compositions of the present invention is a branched block copolymer having a structure composed of hydrophobic blocks, to which blocks are attached, in particular via bifunctional units, a certain number of more hydrophilic blocks. These copolymers exhibit at least two glass transition temperatures.

They are disclosed in particular in Patent Application WO 00/40628.

The branched block copolymers described above are provided, for example, under the names EX-SDR-26® and EX-SDR-45® by Goodrich.

These copolymers have the following composition:
- from 26 to 36 mol % of acrylic acid
- from 27.5 to 30.5 mol % of n-butyl acrylate
- from 33.3 to 45.3 mol % of methacrylic acid
- from 0.48 to 0.92 mol % of allyl methacrylate The most hydrophobic blocks have a molecular weight of 10 000 to 100 000 and the most hydrophilic blocks have a molecular weight of 1 000 to 100 000 daltons.

The fixing film-forming polymers above are preferably used in the anionic form, that is to say in the salt form resulting from the partial or complete neutralization of the (meth) acrylic acid groups. The neutralization agent can be any physiologically acceptable inorganic or organic base which does not interfere unfavourably with the thickening system. Mention may be made, by way of examples of preferred neutralization agent, of 2-amino-2-methyl-1-propanol or sodium hydroxide.

The cosmetically acceptable medium is preferably an aqueous or aqueous/alcoholic medium and in particular an aqueous medium comprising the fixing branched block polymer or polymers in the dissolved state.

The liquid phase preferably comprises between 0.1 and 10% by weight and in particular between 0.5 and 5% by weight of fixing branched block polymer with respect to the total weight of the liquid phase.

The fixing film-forming polymers (b) used in combination with the fixing film-forming polymer or polymers (a) described above are preferably chosen from the cationic, anionic, nonionic or amphoteric fixing polymers listed below. The choice of these polymers is made so as to obtain a styling composition in the mousse form.

The cationic fixing polymers which can be used according to the present invention are preferably chosen from polymers comprising primary, secondary, tertiary and/or quaternary amine groups forming part of the polymer chain or directly bonded to the latter and having a number-average molecular mass of between 500 and approximately 5 000 000 and preferably between 1 000 and 3 000 000.

Mention may more particularly be made, among these polymers, of the following cationic polymers:

(1) homopolymers or copolymers derived from acrylic or methacrylic esters or amides comprising units corresponding $$-CH_2-\underset{\underset{\underset{\underset{R_2}{\diagdown}\underset{R_1}{N}}{A}}{\overset{|}{O}}}{\overset{R_3}{\overset{|}{C}}}- \qquad -CH_2-\underset{\underset{\underset{R_5-\overset{|}{N^+}-R_4}{A}}{\overset{|}{O}}}{\overset{R_3}{\overset{|}{C}}}-X^- \qquad -CH_2-\underset{\underset{\underset{R_5-\overset{|}{N^+}-R_4}{A}}{\overset{|}{NH}}}{\overset{R_3}{\overset{|}{C}}}-X^-$$
$$\hspace{6em}\underset{\hspace{2em}R_6}{} \hspace{6em}\underset{\hspace{2em}R_6}{}$$

to at least one of the following formulae:
in which:
$R_1$ and $R_2$ each independently represent a hydrogen atom or a $C_{1-6}$ alkyl group;
$R_3$ denotes a hydrogen atom or a $CH_3$ group;

A is a linear or branched alkyl group comprising from 1 to 6 carbon atoms or a hydroxyalkyl group comprising from 1 to 4 carbon atoms;

$R_4$, $R_5$ and $R_6$ each independently represent an alkyl group having from 1 to 18 carbon atoms or a benzyl group;

X denotes a methyl sulphate or halide anion, such as chloride or bromide.

The copolymers of the family (1) additionally comprise one or more units deriving from comonomers chosen from the family of the acrylamides, methacrylamides, diacetone acrylamides, acrylamides and methacrylamides substituted on the nitrogen by lower alkyl groups, (meth)acrylic acids or their esters, vinyllactams, such as vinylpyrrolidone or vinylcaprolactam, or vinyl esters.

Thus, mention may be made, among these copolymers of the family (1), of:

copolymers of acrylamide and of dimethylaminoethyl methacrylate quaternized with dimethyl sulphate or with a methyl halide, such as that sold under the name Hercofloc® by Hercules, copolymers of acrylamide and of methacryloyloxy-ethyltrimethylammonium chloride disclosed, for example, in Patent Application EP-A-080 976 and sold under the name Bina Quat® P100 by Ciba-Geigy, the copolymer of acrylamide and of methacryloyl-oxyethyltrimethylammonium methyl sulphate sold under the name Reten® by Hercules, optionally quaternized vinylpyrrolidone/dialkylaminoalkyl acrylate or methacrylate copolymers, such as the products sold under the name Gafquat® by ISP, such as, for example, Gafquat® 734 or Gafquat® 755, or else the products named <<Copolymer® 845, 958 and 937>>. These polymers are disclosed in detail in French Patents FR 2 077 143 and FR 2 393 573, dimethylaminoethyl methacrylate/vinylcaprolactam/vinylpyrrolidone terpolymers, such as the product sold under the name Gaffix® VC 713 by ISP, and quaternized dimethylaminopropylmethacrylamide/vinylpyrrolidone copolymers, such as in particular the product sold under the name Gafquat® HS 100 by ISP.

(2) quaternized polysaccharides, disclosed more particularly in U.S. Pat. No. 3,589,578 and U.S. Pat. No. 4,031,307, such as guar gums comprising cationic trialkylammonium groups. Such products are sold in particular under the names Jaguar C13 S, Jaguar C 15 and Jaguar C 17 by Meyhall.

(3) quaternary copolymers of vinylpyrrolidone and of vinylimidazole, such as the products sold by BASF under the name Luviquat TFC.

(4) chitosans and their salts, such as chitosan acetate, lactate, glutamate, gluconate or pyrrolidonecarboxylate.

Mention may be made, among these compounds, of the chitosan having a degree of deacetylation of 90.5% by weight sold under the name Kytan Brut Standard by Aber Technologies or the chitosan pyrrolidonecarboxylate sold under the name Kytamer® PC by Amerchol.

(5) cationic cellulose derivatives, such as copolymers of cellulose or of cellulose derivatives grafted with a water-soluble monomer comprising a quaternary ammonium, which are disclosed in particular in patent U.S. Pat. No. 4,131,576, such as hydroxyalkylcelluloses, for example hydroxymethylcelluloses, hydroxyethylcelluloses and hydroxypropylcelluloses, grafted in particular with a methacryloyloxyethyltrimethylammonium, methacrylamido-propyltrimethylammonium or dimethyldiallylammonium salt.

These polymers are sold in particular under the names Celquat® L200 and Celquat® H100 by National Starch.

The anionic fixing polymers generally used are polymers comprising groups derived from carboxylic acid, from sulphonic acid or from phosphoric acid and have a number-average molecular mass of between approximately 500 and 5 000 000.

The carboxyl groups are contributed by unsaturated carboxylic mono- or diacid monomers such as those corresponding to the formula:

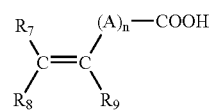

in which n is an integer from 0 to 10,

A denotes a methylene group, optionally connected to the carbon atom of the unsaturated group or to the neighbouring methylene group when n is greater than 1 via a heteroatom, such as oxygen or sulphur, $R_7$ denotes a hydrogen atom or a phenyl or benzyl group, $R_8$ denotes a hydrogen atom or a lower alkyl or carboxyl group, and $R_9$ denotes a hydrogen atom, a lower alkyl group or a —$CH_2$—COOH, phenyl or benzyl group.

In the abovementioned formula, a lower alkyl group preferably denotes a group having 1 to 4 carbon atoms and in particular the methyl and ethyl groups.

The preferred anionic fixing polymers comprising carboxyl groups according to the invention are:

A) Homo- or copolymers of acrylic or methacrylic acid or their salts and in particular the products sold under the names Versicol® E or K by Allied Colloid and Ultrahold® by BASF, the copolymers of acrylic acid and of acrylamide sold in the sodium salt form under the names Reten® 421, 423 or 425 by Hercules, and the sodium salts or polyhydroxycarboxylic acids.

B) Copolymers of acrylic or methacrylic acid with a monoethylenic monomer, such as ethylene, styrene, vinyl esters or esters of acrylic or methacrylic acid, optionally grafted onto a polyalkylene glycol, such as polyethylene glycol, and optionally crosslinked. Such polymers are disclosed in particular in French Patent FR 1 222 944 and German Patent Application DE 2 330 956, the copolymers of this type comprising, in their chain, an optionally N-alkylated and/or N-hydroxyalkylated acrylamide unit, such as disclosed in particular in Luxembourgian Patent Applications Nos. 75370 and 75371 and provided under the name Quadramer® by American Cyanamid. Mention may also be made of copolymers of acrylic acid and of $C_1$-$C_4$ alkyl methacrylate and terpolymers of vinylpyrrolidone, of acrylic acid and of $C_1$-$C_{20}$ alkyl methacrylate, for example lauryl methacrylate, such as that sold by ISP under the name Acrylidone® LM, and methacrylic acid/ethyl acrylate/tert-butyl acrylate terpolymers, such as the products sold under the name Luvimer® 100 P by BASF.

C) Copolymers derived from crotonic acid, such as those comprising, in their chain, vinyl acetate or propionate units and optionally other monomers, such as allyl or methallyl esters, vinyl ether or vinyl ester of a linear or branched saturated carboxylic acid comprising a long hydrocarbonaceous chain, such as those comprising at least 5 carbon atoms, it being possible for these polymers optionally to be grafted and crosslinked, or alternatively another monomer which is a vinyl, allyl or methallyl ester of an _- or _-cyclic carboxylic acid. Such polymers are disclosed, inter alia, in French Patents FR 1 222 944, FR 1 580 545, FR 2 265 782, FR 2 265 781, FR 1 564 110 and FR 2 439 798. Commercial products coming within this class are the resins 28-29-30, 26-13-14 and 28-13-10 sold by National Starch.

D) Copolymers derived from $C_4$-$C_8$ monounsaturated carboxylic acids or anhydrides chosen from:

copolymers comprising (i) one or more maleic, fumaric or itaconic acids or anhydrides and (ii) at least one monomer chosen from vinyl esters, vinyl ethers, vinyl halides, phenylvinyl derivatives, or acrylic acid and its esters, the anhydride functional groups of these copolymers optionally being monoesterified or monoamidated. Such polymers are disclosed in particular in U.S. Pat. Nos. 2,047,398, 2,723,248 and 2,102,113 and Patent GB 839 805. Commercial products are in particular those sold under the names Gantrez® AN or ES by ISP.

copolymers comprising (i) one or more maleic, citraconic or itaconic anhydride units and (ii) one or more monomers chosen from allyl or methallyl esters, optionally comprising one or more acrylamide, methacrylamide, _-olefin, acrylic or methacrylic ester, acrylic or methacrylic acid, or vinylpyrrolidone groups in their chain, the anhydride functional groups of these copolymers optionally being monoesterified or monoamidated.

These polymers are, for example, disclosed in French Patents FR 2 350 384 and FR 2 357 241 of the Applicant Company.

E) Polyacrylamides comprising carboxylate groups.

The polymers comprising sulpho groups are polymers comprising vinylsulphonic, styrenesulphonic, naphthalenesulphonic or acrylamidoalkylsulphonic units.

These polymers can in particular be chosen from:

salts of polyvinylsulphonic acid having a molecular mass of between approximately 1 000 and 100 000, and copolymers with an unsaturated comonomer, such as acrylic acid or methacrylic acid and their esters, acrylamide or its derivatives, vinyl ethers and vinylpyrrolidone.

salts of polystyrenesulphonic acid, such as the sodium salts sold, for example, under the names Flexan® 130 and Flexan® 500 by National Starch. These compounds are disclosed in Patent FR 2 198 719.

salts of polyacrylamidosulphonic acids, such as those mentioned in patent U.S. Pat. No. 4,128,631 and more particularly the polyacrylamidoethylpropanesulphonic acid sold under the name Cosmedia Polymer® HSP 1180 by Henkel.

The amphoteric fixing polymers which can be used in the styling mousses of the present invention can be chosen from polymers comprising B and C units distributed randomly in the polymer chain, where B denotes a unit deriving from a monomer comprising at least one basic nitrogen atom and C denotes a unit deriving from a monomer comprising one or more carboxyl or sulpho groups. The amphoteric fixing polymers can also comprise zwitterionic units of carboxybetaine or sulphobetaine type.

They can also be polymers comprising a cationic main chain comprising primary, secondary, tertiary or quaternary amine groups, at least one among which carries, via a hydrocarbonaceous radical, a carboxylic acid or sulphonic acid group. The amphoteric fixing polymers can also have an anionic chain derived from _,_-unsaturated carboxylic acids, one of the carboxyl groups of which has been reacted with a polyamine comprising one or more primary amine groups.

The amphoteric fixing polymers corresponding to the definition given above are chosen in particular from the following polymers:

(1) polymers resulting from the copolymerization of a monomer derived from a vinyl compound carrying a carboxyl group, such as more particularly acrylic aced, methacrylic acid, maleic acid or _-chloroacrylic acid, and of a basic monomer derived from a substituted vinyl compound comprising at least one basic atom, such as more particularly dialkylaminoalkyl methacrylate and acrylate or dialkylaminoalkyl-methacrylamide and -acrylamide. Such compounds are disclosed in U.S. Pat. No. 3,836,537.

(2) polymers comprising units deriving:

(a) from at least one monomer chosen from acrylamides or methacrylamides substituted on the nitrogen atom by an alkyl group, (b) from at least one acidic comonomer comprising one or more reactive carboxyl groups, and (c) from at least one basic comonomer, such as esters comprising primary, secondary, tertiary or quaternary amine substituents of acrylic and methacrylic acids and the quaternization product of dimethylaminoethyl methacrylate with dimethyl or diethyl sulphate.

The N-substituted acrylamides or methacrylamides are in particular compounds in which the alkyl groups comprise from 2 to 12 carbon atoms and more particularly N-ethylacrylamide, N-tert-butylacrylamide, N-tert-octylacrylamide, N-octylacrylamide, N-decylacrylamide or N-dodecylacrylamide, and the corresponding methacrylamides.

The acidic comonomers are more particularly chosen from acrylic, methacrylic, crotonic, itaconic, maleic or fumaric acids and alkyl monoesters having 1 to 4 carbon atoms of maleic or fumaric acids or anhydrides.

The preferred basic comonomers are aminoethyl, butylaminoethyl, N,N'-dimethylaminoethyl or N-tert-butylaminoethyl methacrylates.

Use is particularly made of the copolymers for which the CTFA name (4th Ed., 1991) is Octylacrylamide/acrylates/butylaminoethyl methacrylate copolymer, such as the products sold under the name Amphomer® or Lovocryl® 47 by National Starch.

(3) partially or completely alkylated and crosslinked polyaminoamides deriving from polyaminoamides of general formula:

—(CO—$R_{10}$—CO-Z-)- in which $R_{10}$ represents a divalent group derived from a saturated dicarboxylic acid, from an aliphatic mono- or dicarboxylic acid comprising an ethylenic double bond, from an ester of a lower alkanol having 1 to 6 carbon atoms of these acids, or from a group deriving from the condensation of any one of the said acids with a bisprimary or bissecondary amine, and Z denotes a group deriving from a bisprimary, mono- or bissecondary polyalkylenepolyamine and preferably represents:

a) in the proportions of 60 to 100 mol %, the group

—NH—[($CH_2$)$_x$—NH]$_p$— where x=2 and p=2 or 3, or else x=3 and p=2 this group deriving from diethylenetriamine, triethylenetetraamine or dipropylenetriamine;

b) in the proportions of 0 to 40 mol %, the group

—NH—[($CH_2$)$_x$—NH]$_p$— where x=2 and p=1 and which derives from ethylenediamine, or the group deriving from piperazine:

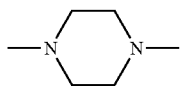

c) in the proportions of 0 to 20 mol %, the group

deriving from hexamethylenediamine, these polyaminoamides being crosslinked by an addition reaction of a bifunctional crosslinking agent chosen from epihalohydrins, diepoxides, dianhydrides or bisunsaturated derivatives, by means of 0.025 to 0.35 mol of crosslinking agent per amine group of the polyaminoamide, and alkylated by reaction with acrylic acid, chloroacetic acid or an alkanesultone or their salts.

The saturated carboxylic acids are preferably chosen from acids having 6 to 10 carbon atoms, such as adipic, 2,2,4-trimethyladipic and 2,4,4-trimethyladipic, or terephthalic acids, or the acids comprising an ethylenic double bond, such as, for example, acrylic, methacrylic or itaconic acids.

The alkanesultones used in the alkylation are preferably propane- or butanesultone and the salts of the alkylating agents are preferably the sodium or potassium salts.

(4) Polymers comprising zwitterionic units of formula;

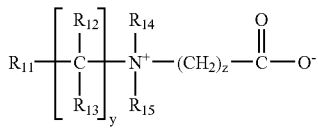

in which $R_{11}$ denotes a polymerizable unsaturated group, such as an acrylate, methacrylate, acrylamide or methacrylamide group, y and z each represent an integer from 1 to 3, $R_{12}$ and $R_{13}$ represent a hydrogen atom or a methyl, ethyl or propyl group, and $R_{14}$ and $R_{15}$ represent a hydrogen or an alkyl group such that the sum of the carbon atoms in $R_{14}$ and $R_{15}$ does not exceed 10.

The polymers comprising such units can also comprise units derived from nonzwitterionic monomers, such as dimethyl- or diethylaminoethyl acrylate or methacrylate or alkyl acrylates or methacrylates, acrylamides or methacrylamides, or vinyl acetate.

Mention may be made, by way of example, of methyl methacrylate/dimethylcarboxymethylammonio-
ethylmethacrylate copolymers, such as the product sold under the name Diaformer® Z301 by Sandoz.

(5) polymers derived from chitosan comprising monomer units corresponding to the following formulae:

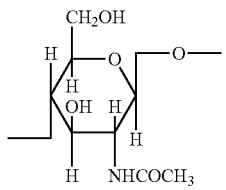

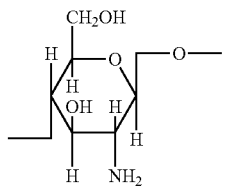

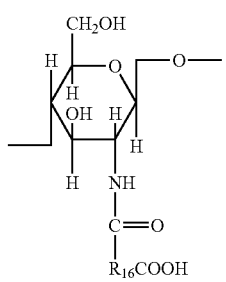

the unit (A) being present in proportions of between 0 and 30%, the unit (B) in proportions of between 5 and 50% and the unit (C) in proportions of between 30 and 90%, it being understood that, in this unit (C), $R_{16}$ represents a group of formula:

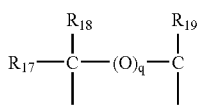

in which, if q=0, $R_{17}$, $R_{18}$ and $R_{19}$, which are identical or different, each represent a hydrogen atom, a methyl, hydroxyl, acetoxy or amino residue, a monoalkylamine residue or a dialkylamine residue, optionally interrupted by one or more nitrogen atoms and/or optionally substituted by one or more amino, hydroxyl, carboxyl, alkylthio or sulpho groups, or an alkylthio residue in which the alkyl group carries an amino residue, at least one of the $R_{17}$, $R_{18}$ and $R_{19}$ groups being, in this case, a hydrogen atom;

or, if q=1, $R_{17}$, $R_{18}$ and $R_{19}$ each represent a hydrogen atom, and the salts formed by these compounds with bases or acids.

(6) Polymers obtained by N-carboxylation of chitosan, such as N-(carboxymethyl)chitosan or N-(carboxybutyl)chitosan, sold under the name Evalsan® by Jan Dekker.

(7) The polymers disclosed in French Patent FR 1 400 366,

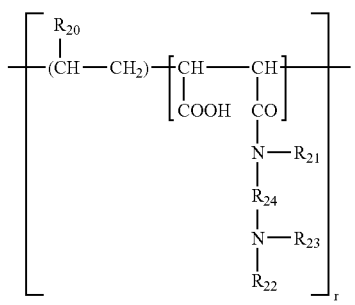

corresponding to the formula in which $R_{20}$ represents a hydrogen atom or a $CH_3O$, $CH_3CH_2O$ or phenyl group, $R_{21}$ denotes a hydrogen atom or a lower alkyl group, such as methyl and ethyl, $R_{22}$ denotes a hydrogen atom or a lower $C_1$-$C_6$ alkyl group, such as methyl and ethyl, $R_{23}$ denotes a lower $C_1$-$C_6$ alkyl group, such as methyl or ethyl, or a group corresponding to the formula: —$R_{24}$—$N(R_{22})_2$, $R_{24}$ representing a —$CH_2$—$CH_2$—, —$CH_2$—$CH_2$—$CH_2$— or —$CH_2$—$CH(CH_3)$— group and $R_{22}$ having the meanings mentioned above.

(8) Amphoteric polymers of the -D-X-D-X— type chosen from:

(a) polymers obtained by reaction of chloroacetic acid or sodium chloroacetate with compounds comprising at least one unit of formula:

-D-X-D-X-D- where D denotes a group

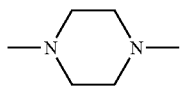

and X denotes the symbol E or E', E or E', which are identical or different, denoting a bivalent group which is a straight- or branched-chain alkylene group comprising up to 7 carbon atoms in the main chain which is unsubstituted or substituted by hydroxyl groups and which can additionally comprise oxygen, nitrogen or sulphur atoms or 1 to 3 aromatic and/or heterocyclic rings; the oxygen, nitrogen and sulphur atoms being present in the form of ether, thioether, sulphoxide, sulphone, sulphonium, alkylamine or alkenylamine groups or hydroxyl, benzylamine, amine oxide, quaternary ammonium, amides imide, alcohol, ester and/or urethane groups.

(b) polymers of formula:

-D-X-D-X-

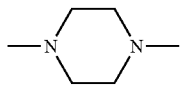

where D denotes a group and X denotes the symbol E or E' and E' at least once, E having the meaning indicated above and E' being a bivalent group which is a straight- or branched-chain alkylene group having up to 7 carbon atoms in the main chain which is substituted or unsubstituted by one or more hydroxyl groups and which comprises one or more nitrogen atoms, the nitrogen atom being substituted by an alkyl chain optionally interrupted by an oxygen atom and necessarily comprising one or more carboxyl functional groups or one or more hydroxyl functional groups and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine, such as N,N-dimethylamino-propylamine, or by semiesterification with an N,N-dialkanolamine. These copolymers can also comprise other vinyl comonomers, such as vinylcaprolactam.

The nonionic fixing polymers are chosen, for example, from:

vinylpyrrolidone homopolymers, copolymers of vinylpyrrolidone and of vinyl acetate, polyalkyloxazolines, such as the polyethyloxazolines provided by Dow Chemical under the names PEOX® 50 000, PEOX® 200 000 and PEOX® 500 000, vinyl acetate homopolymers, such as the product provided under the name Appretan® EM by Hoechst or the product provided under the name of Rhodopas® A 012 by Rhône-Poulenc, copolymers of vinyl acetate and of acrylic ester, such as the product provided under the name of Rhodopas® AD 310 from Rhône-Poulenc, copolymers of vinyl acetate and of ethylene, such as the product provided under the name of Appretan® TV by Hoechst, copolymers of vinyl acetate and of maleic ester, for example of dibutyl maleate, such as the product provided under the name of Appretan® MB EXTRA by Hoechst, copolymers of ethylene and of maleic anhydride, poly(alkyl acrylate)s and poly(alkyl methacrylate)s, such as the product provided under the name Micropearl® RQ 750 by Matsumoto or the product provided under the name Luhydran® A 848 S by BASF, acrylic ester copolymers, such as, for example, copolymers of alkyl acrylates and of alkyl methacrylates, such as the products provided by Rohm & Haas under the names Primal® AC-261 K and Eudragit® NE 30 D, by BASF under the names Acronal® 601, Luhydran® LR 8833 or 8845, or by Hoechst under the names Appretan® N9212 and N9213;

copolymers of acrylonitrile and of a nonionic monomer chosen, for example, from butadiene and alkyl (meth) acrylates; mention may be made of the products provided under the names Nipol® LX 531 B by Nippon Zeon or those provided under the name CJ 0601 B by Rohm & Haas, polyurethanes, such as the products provided under the names Acrysol® RM 1020 or Acrysol® RM 2020 by Rohm & Haas or the products Uraflex® XP 401 and Uraflex® XP 402 UZ provided by DSM Resins, polyamides, such as the product Estapor® LO 11 provided by Rhône-Poulenc, chemically modified or unmodified nonionic guar gums. The unmodified guar gums are, for example, the products sold under the name Vidogum® GH 175 by Unipectine and under the name Jaguar® C by Meyhall. The modified guar gums are preferably modified by $C_{1-6}$ hydroxyalkyl groups, preferably by hydroxymethyl, hydroxyethyl, hydroxypropyl and hydroxybutyl groups. Such nonionic guar gums optionally modified by hydroxyalkyl groups are, for example, sold under the trade names Jaguar® HP8, Jaguar® HP60, Jaguar® HP120, Jaguar® DC293 and Jaguar® HP105 by Meyhall or under the name Galactosol® 4H4FD2 by Aqualon.

Use may also be made, as additional fixing polymers (b), of film-forming polymers of grafted silicone type comprising a polysiloxane part and a part composed of a non-silicone organic chain, one of the two parts constituting the main chain of the polymer and the other being grafted onto the said main chain.

These polymers are disclosed, for example, in Patent Applications EP-A-0 412 704, EP-A-0 412 707, EP-A-0 640 105 and WO 95/00578, EP-A-0 582 152 and WO 93/23009 and U.S. Pat. No. 4,693,935, U.S. Pat. No. 4,728,571 and U.S. Pat. No. 4,972,037.

These polymers are preferably anionic or nonionic.

Such polymers are, for example, the copolymers capable of being obtained by radical polymerization from the mixture of monomers formed
a) from 50 to 90% by weight of tert-butyl acrylate,
b) from 0 to 40% by weight of acrylic acid,

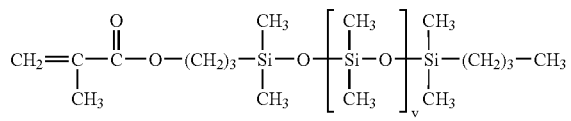

c) from 5 to 40% by weight of a silicone macromer of formula where v is a number ranging from 5 to 700, the percentages by weight being calculated with respect to the total weight of the monomers.

Other examples of grafted silicone polymers are in particular polydimethylsiloxanes (PDMSs) onto which are grafted, via a connecting link of thiopropylene type, mixed polymer units of the poly(meth)acrylic acid type and of the poly(alkyl (meth)acrylate) type and polydimethylsiloxanes (PDMSs) onto which are grafted, via a connecting link of thiopropylene type, polymer units of the poly(isobutyl (meth)acrylate) type.

It is also possible to use, as additional fixing polymers (b) in the styling compositions of the present invention, functionalized or non-functionalized and silicone-comprising or non-silicone-comprising polyurethanes.

The polyurethanes particularly targeted by the present invention are those disclosed in the documents EP-A-0 751 162, EP-A-0 637 600, FR 2 743 297 and EP 0 648 485, of which the Applicant Company is Proprietor, and Applications EP-A-0 656 021 or WO 94/03510 of BASF and Application EP-A-0 619 111 of National Starch.

These Nixing polymers (b), other than the fixing branched block polymers (a) used in the aerosol mousses of the present invention, are preferably present in the styling compositions of the present invention in a proportion of 0.1 to 10% by weight, and in particular in a proportion of 0.1 to 5% by weight, with respect to the total weight of the liquid phase.

The styling mousses packaged in an aerosol device of the present invention can comprise one or more surface-active agents. These surface-active agents promote the formation of fine mousses having a degree of stability necessary for good distribution over the hair.

The surface-active agents can be nonionic, cationic, anionic or zwitterionic surface-active agents.

When nonionic surface-active agents are used, the latter are chosen in particular from fatty alcohols, _-diols, ($C_1$-$C_{20}$) alkylphenols or acids which are polyethoxylated, polypropoxylated or polyglycerolated, having a fatty chain comprising, for example, from 8 to 18 carbon atoms, it being possible for the number of ethylene oxide or propylene oxide groups to range in particular from 2 to 50 and it being possible for the number of glycerol groups to range in particular from 2 to 30. Mention may also be made of copolymers of ethylene and propylene oxide, condensates of ethylene and propylene oxide with fatty alcohols, polyethoxylated fatty amides preferably having from 2 to 30 mol of ethylene oxide, polyglycerolated fatty amides comprising on average from 1 to 5 and in particular from 1.5 to 4 glycerol groups, polyethoxylated fatty amines Preferably having 2 to 30 mol of ethylene oxide, sorbitan ethoxylated fatty acid esters having from 2 to 30 mol of ethylene oxide, sucrose fatty acid esters, polyethylene glycol esters of fatty acids, ($C_6$-$C_{24}$)alkylpolyglycosides, N—($C_6$-$C_{24}$)alkylglucamine derivatives, amine oxides, such as oxides of ($C_{10}$-$C_{14}$)alkylamines or N—($C_{10}$-$C_{14}$)acylaminopropyl-orpholine oxides, and mixtures of these.

These nonionic surface-active agents are well known compounds and are described, for example, in <<Handbook of Surfactants>> by M. R. Porter, published by Blackie & Son (Glasgow and London), 1991, pp 116-178.

Mention may in particular be made, by way of examples of anionic surface-active agents, of the salts, in particular the alkali metal salts, such as the sodium salts, the ammonium salts, the amine salts, the aminoalcohol salts or the alkaline earth metal salts, for example the magnesium salts, of the following compounds: alkyl sulphates, alkyl ether sulphates, alkylamido ether sulphates, alkylarylpolyether sulphates, monoglyceride sulphates, alkylsulphonates, alkyl phosphates, alkylamidesulphonates, alkylarylsulphonates, _-olefinsulphonates, paraffinsulphonates, alkyl sulphosuccinates, alkyl ether sulphosuccinates, alkylamidesulphosuccinates, alkyl sulphoacetates, acylsarcosinates and acylglutamates, the alkyl or acyl groups of all these compounds comprising from 6 to 24 carbon atoms and the aryl group preferably denoting a phenyl or benzyl group.

Use may also be made of $C_6$-$C_{24}$ alkyl esters of polyglycosidecarboxylic acids, such as alkyl glucosidecitrates, alkyl polyglycosidetartrates and alkyl polyglycosidesulphosuccinates; alkyl sulphosuccinamates, acylisethionates and N-acyltaurates, the alkyl or acyl group of all these compounds comprising from 12 to 20 carbon atoms. Mention may also be made, among the anionic surfactants which can also be used, of acyliactylates, the acyl group of which comprises from 8 to 20 carbon atoms.

In addition, mention may also be made of alkyl-D-galactosideuronic acids and their salts, and polyoxyalkylenated ($C_6$-$C_{24}$)alkyl ether carboxylic acids, polyoxyalkylenated ($C_6$-$C_{24}$)alkyl($C_6$-$C_{24}$)aryl ether carboxylic acids, polyoxyalkylenated ($C_6$-$C_{24}$)alkylamido ether carboxylic acids and their salts, in particular those comprising from 2 to 50 ethylene oxide groups, and their mixtures.

The amphoteric surface-active agents can in particular be derivatives of aliphatic secondary or tertiary amines in which the aliphatic group is a linear or branched chain comprising from 8 to 22 carbon atoms and comprising at least one water-solubilizing anionic group, such as, for example, a carboxylate, sulphonate, sulphate, phosphate or phosphonate group; mention may also be made of ($C_8$-$C_{20}$)alkyl betaines, sulphobetaines, ($C_8$-$C_{20}$)alkyl amido($C_6$-$C_8$)alkyl betaines or ($C_8$-$C_{20}$)alkyl amido($C_6$-$C_8$)alkyl sulphobetaines, and their mixtures.

Mention may be made, among the amine derivatives, of the products sold under the name Miranol®, such as those disclosed in U.S. Pat. No. 2,528,378 and U.S. Pat. No. 2,781,354 and classified in the CTFA dictionary, 3rd edition, 1982, under the names Amphocarboxyglycinate and Amphocarboxypropionate, corresponding respectively to the formulae (a) and (b):

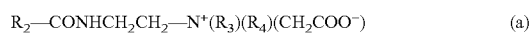

in which:
$R_2$ represents an alkyl group derived from an acid $R_2$—COOH present in hydrolyzed coconut oil or a heptyl, nonyl or undecyl group,
$R_3$ represents a _-hydroxyethyl group, and
$R_4$ represents a carboxymethyl group; and

in which:

B represents —CH$_2$CH$_2$OX',

C represents —(CH$_2$)$_z$—Y', with z=1 or 2,

X' represents the —CH$_2$CH$_2$—COOH group or a hydrogen atom,

Y' represents —COOH or the —CH$_2$—CHOH—SO$_3$H group,

R$_2$' represents an alkyl group of an acid R$_2$'—COOH present in coconut oil or in hydrolyzed linseed oil, an alkyl group, in particular a C$_{17}$ alkyl group and its iso form, or an unsaturated C$_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylamphodipropionate, disodium caprylamphodipropionate, lauroamphodipropionic acid and cocoamphodipropionic acid.

Mention may be made, by way of example, of the cocoamphodiacetate sold under the trade name Miranol® C2M concentrate by Rhodia.

The concentration of these surface-active agents in the aerosol mousses of the present invention is preferably between 0.1 and 10% by weight, and in particular between 0.1 and 4% by weight, with respect to the total weight of the liquid phase.

The styling mousses of the present invention can be packaged in aerosol devices in the presence of any propellant conventionally employed in the preparation of aerosol compositions. Use will preferably be made of propellants which are insoluble or partially soluble in the liquid phase, such as dimethyl ether, C$_{3-5}$ alkanes, 1,1-difluoroethane, mixtures of dimethyl ether and of C$_{3-5}$ alkanes, and mixtures of 1,1-difluoroethane and of dimethyl ether and/or of C$_{3-5}$ alkanes.

Preference is very particularly given to the use, as propellant for the aerosol mousses of the present invention, of C$_{3-5}$ alkanes and in particular propane, n-butane and isobutane.

The ratio by weight of the liquid phase to the propellant of the aerosol mousses of the present invention is preferably between 70/30 and 98/2 and in particular between 85/15 and 96/4.

Another subject-matter of the invention is a styling process which consists in applying, to the hair, an appropriate amount of the styling composition according to the invention, in spreading the composition over the hair until the mousse has disappeared and in then drying the hair or allowing it to dry after it has been given the desired form.

The formulation examples illustrate the present invention without, however, limiting it.

EXAMPLES 1 TO 6

| Aerosol styling mousses | | | | | | |
|---|---|---|---|---|---|---|
| Ingredients of the liquid phase (in % by weight) | 1 | 2 | 3 | 4 | 5 | 6 |
| EX-SDR-26 ®[a] | 2 | 2 | 1 | 2 | 2 | 0.5 |
| Luvimer MAE ®[b] | — | — | — | 3 | — | — |
| Acrylidone ® LM[c] | — | — | — | — | 2 | 1 |
| Celquat ® LOR[d] | — | 0.5 | 0.5 | — | — | — |
| DC 2 1388 ®[e] | — | 5 | 5 | 5 | 5 | 10 |
| Tego-betaine ® HS[f] | — | — | 0.5 | — | — | — |
| Brij ® 30[g] | — | — | 0.5 | — | — | — |

| Aerosol styling mousses | | | | | | |
|---|---|---|---|---|---|---|
| Ingredients of the liquid phase (in % by weight) | 1 | 2 | 3 | 4 | 5 | 6 |
| Ethanol | 8.2 | — | — | 8.2 | 8.2 | — |
| Water | q.s. for 100 g | q.s. for 100 g | q.s. for 100 g | q.s. for 100 g | q.s. for 100 g | q.s. for 100 g |
| Liquid phase/ propellant ratio[h] | 95/5 | 95/5 | 95/5 | 95/5 | 95/5 | 95/5 |

[a] branched block copolymer sold by Goodrich
[b] copolymer of methacrylic acid (50) and of ethyl acrylate (50) sold as a 30% aqueous disperion by BASF
[c] terpolymer of vinylpyrrolidone (23), of acrylic acid (68) and of lauryl methacrylate (9) sold by ISP
[d] copolymer of hydroxyethylcellulose and of diallyl-dimethylammonium chloride sold by National Starch
[e] _,_-dihydroxypolydimethylsiloxane (10)/cyclopenta-dimethylsiloxane (90) as a 60% aqueous emulsion sold by Dow Corning
[f] cocoylamidopropyl betaine (25)/glyceryl monolaurate (5) mixture at 30% in water sold by Goldschmidt
[g] lauryl alcohol ethoxylated with 4 mol of ethylene oxide sold by Uniqema
[h] isobutane (56)/butane (24)/propane (20) mixture sold under the name Aerogaz ® 3.2 N by Atochem

The invention claimed is:

1. Composition in the form of a styling mousse, packaged in an aerosol device, comprising
   a liquid phase comprising, in an aqueous or aqueous/alcoholic medium,
   (a) at least one fixing film-forming polymer comprising 26 to 36 mol % of acrylic acid, 27.5 to 30.5 mol % of n-butyl acrylate, 33.3 to 45.3 mol % of methacrylate acid and 0.48 to 0.92 mol % of allyl methacrylate, and
   (b) at least one other fixing film-forming polymer other than the fixing film-forming polymer of (a), said at least one other fixing film-forming polymer being a copolymer of methacrylic acid (50) and ethyl acrylate (50) or being a terpolymer of vinylpyrrolidone (23), acrylic acid (68) and lauryl methacrylate (9),
   the fixing film-forming polymer of (a) being present in an amount of 0.5 to 5% by weight with respect to the total weight of the liquid phase and the other fixing film-forming polymer of (b) being present in an amount of 0.1 to 5% by weight with respect to the total weight of the liquid phase;
   one or more surface-active agents chosen from nonionic, cationic, anionic and zwitterionic surface-active agents in an amount of 0.1 to 4% by weight with respect to the total weight of the liquid phase; and
   at least one propellant selected from the group consisting of dimethyl ether, C$_{3-5}$ alkanes, 1,1-difluoroethane, a mixture of dimethyl ether and C$_{3-5}$ alkanes, and a mixture of 1,1-difluoroethane, dimethyl ether and optionally C$_{3-5}$ alkanes, wherein the ratio by weight of the liquid phase to the propellant is between 85/15 and 96/4.

2. Styling composition according to claim 1, characterized in that the propellant is chosen from C$_{3-5}$ alkanes.

3. Styling process which consists in applying, to the hair, an appropriate amount of the styling composition according to claim 1, in spreading the composition over the hair until the mousse has disappeared and in then drying the hair or allowing it to dry after it has been given the desired form.

4. The styling composition of claim 1 wherein said lipid phase comprises an aqueous medium.

* * * * *